(12) United States Patent
Lavallee

(10) Patent No.: US 7,691,108 B2
(45) Date of Patent: Apr. 6, 2010

(54) INSTRUMENT FOR LOCATING THE POSITION OF A CUTTING PLANE

(75) Inventor: Stéphane Lavallee, Saint Martin d'Uriage (FR)

(73) Assignee: Perception Raisonnement Action en Medecine, La Tronche (FR)

( * ) Notice: Subject to any disclaimer, the term of this patent is extended or adjusted under 35 U.S.C. 154(b) by 1111 days.

(21) Appl. No.: 10/547,998

(22) PCT Filed: Mar. 11, 2004

(86) PCT No.: PCT/FR2004/050103

§ 371 (c)(1),
(2), (4) Date: Dec. 19, 2005

(87) PCT Pub. No.: WO2004/082489

PCT Pub. Date: Sep. 30, 2004

(65) Prior Publication Data

US 2006/0149287 A1   Jul. 6, 2006

(30) Foreign Application Priority Data

Mar. 11, 2003   (FR) .................................. 03 02982

(51) Int. Cl.
*A61F 5/00* (2006.01)
*A61B 17/58* (2006.01)
*A61B 17/60* (2006.01)
*A61B 2/00* (2006.01)

(52) U.S. Cl. .................. 606/87; 606/86 R; 606/90; 606/102

(58) Field of Classification Search .............. 606/102, 606/86 A, 86 B, 79, 82, 87–91, 96, 86 R
See application file for complete search history.

(56) References Cited

U.S. PATENT DOCUMENTS

| 4,180,247 | A | * | 12/1979 | Pfarr, Jr. | ...................... | 256/54 |
| 4,501,266 | A | * | 2/1985 | McDaniel | ..................... | 606/90 |
| 4,841,975 | A | * | 6/1989 | Woolson | ..................... | 600/425 |
| 5,213,112 | A | * | 5/1993 | Niwa et al. | ................. | 600/587 |

(Continued)

FOREIGN PATENT DOCUMENTS

DE   1 190 676 A1   3/2002

*Primary Examiner*—Thomas C Barrett
*Assistant Examiner*—Matthew Lawson
(74) *Attorney, Agent, or Firm*—Leason Ellis LLP

(57) ABSTRACT

A position locating instrument for accurately determining the location of a cutting plane includes a base connected to means capable of determining the position of the instrument. The base includes bent blades 28A to 28D that are flexible enough not to prevent the insertion of plate 24 into opening 36 of a bone cuffing guide. Bent blades 28A to 28D are however rigid enough to maintain lower surface 25 of plate 24 pressed against lower surface 38 of opening 36, with the free ends of bent blades 28A to 28D bearing against upper surface 39 of opening 36. Bent blades 28A to 28D have a sufficient stiffness to provide a sufficient force to oppose displacement of plate 24 that is inserted in opening 36 by pushing lower surface 25 of plate 24 onto lower surface 38 of opening 36. Play between plate 24 and opening 36 are suppressed. By determining the position of plate 24, the position of the cuffing plane is thus directly and accurately obtained.

7 Claims, 1 Drawing Sheet

U.S. PATENT DOCUMENTS

| | | | |
|---|---|---|---|
| 5,263,972 A | 11/1993 | Evans et al. | |
| 5,422,789 A * | 6/1995 | Fisher et al. | 361/719 |
| 5,486,180 A * | 1/1996 | Dietz et al. | 606/87 |
| 5,540,695 A * | 7/1996 | Levy | 606/87 |
| 5,540,696 A * | 7/1996 | Booth et al. | 606/88 |
| 5,601,563 A * | 2/1997 | Burke et al. | 606/86 R |
| 5,669,914 A * | 9/1997 | Eckhoff | 606/88 |
| 5,800,438 A * | 9/1998 | Tuke et al. | 606/90 |
| 5,904,691 A * | 5/1999 | Barnett et al. | 606/130 |
| 5,908,424 A * | 6/1999 | Bertin et al. | 606/88 |
| 5,935,128 A * | 8/1999 | Carter et al. | 606/86 B |
| 6,179,836 B1 * | 1/2001 | Eggers et al. | 606/45 |
| 6,450,978 B1 * | 9/2002 | Brosseau et al. | 600/595 |
| 6,478,799 B1 * | 11/2002 | Williamson | 606/90 |
| 6,514,259 B2 * | 2/2003 | Picard et al. | 606/88 |
| 6,551,325 B2 * | 4/2003 | Neubauer et al. | 606/88 |
| 6,620,168 B1 * | 9/2003 | Lombardo et al. | 606/88 |
| 6,673,077 B1 * | 1/2004 | Katz | 606/88 |
| 6,740,092 B2 * | 5/2004 | Lombardo et al. | 606/88 |
| 6,758,850 B2 * | 7/2004 | Smith et al. | 606/88 |
| 6,932,823 B2 * | 8/2005 | Grimm et al. | 606/130 |
| 7,282,054 B2 * | 10/2007 | Steffensmeier et al. | 606/96 |
| 7,329,076 B2 * | 2/2008 | Hartney et al. | 411/60.1 |
| 7,392,076 B2 * | 6/2008 | Moctezuma de La Barrera | 600/427 |
| 2002/0068942 A1 * | 6/2002 | Neubauer et al. | 606/88 |
| 2002/0095083 A1 | 7/2002 | Cinquin et al. | |
| 2002/0107522 A1 * | 8/2002 | Picard et al. | 606/88 |
| 2004/0102785 A1 * | 5/2004 | Hodorek et al. | 606/87 |
| 2006/0089653 A1 * | 4/2006 | Auger et al. | 606/88 |
| 2007/0219560 A1 * | 9/2007 | Hodorek | 606/88 |
| 2008/0195109 A1 * | 8/2008 | Hunter et al. | 606/87 |

* cited by examiner

INSTRUMENT FOR LOCATING THE POSITION OF A CUTTING PLANE

CLAIM FOR PRIORITY

This application claims the benefit of French Application No. 03/02982, filed Mar. 11, 2003 and Int'l. Application No. PCT/FR2004/050103, filed Mar. 11, 2004 and is incorporated herein by reference.

The present invention relates to an instrument for locating the position of the cutting plane associated with a bone-cutting guide.

In a bone cutting operation, a surgeon generally uses a bone-cutting guide comprising an opening in which a cutting blade is inserted. The opening defines a cutting plane, generally corresponding to the median plane of the opening, and guides the cutting blade in motion along the cutting plane.

It is necessary to accurately know the position of the cutting plane before insertion of the cutting blade. For this purpose, the shape of the cutting guide is preliminarily measured and memorized. It is then enough to determine the position of the cutting guide to obtain the exact position of the cutting plane. A possibility consists of equipping the cutting guide with a rigid body comprising reflective portions, the positions of which are detected by a locating system, for example, infrared.

The rigid body being assembled by a mechanical joint on the cutting guide, the relative position between the cutting guide and the rigid body tends to modify along repeated uses of the cutting guide. It is tedious and difficult to have to regularly check and possibly correct the relative position between the cutting guide and the rigid body to accurately ensure the determination of the position of the cutting plane from the position of the rigid body associated with the cutting guide.

Accordingly, to determine the position of the cutting plane, a plate-shaped locating instrument which is manually inserted into the cutting guide opening similarly to the cutting blade is preferably used. The position of the locating instrument once inserted into the guide is then determined by any known means to determine the position of the cutting plane.

Generally, the position of the locating instrument is determined by attaching a rigid body thereto, the position of the rigid body being obtained by a visual control system. It is relatively easy to check and possibly correct the relative position between the rigid body and the locating instrument to obtain the position of the cutting plane.

However, there may be a play between the locating instrument and the cutting guide opening when the instrument is completely inserted into the cutting guide opening. Such a play may cause an inaccuracy in the cutting plane determination.

The present invention aims at obtaining a locating instrument enabling engagement with no play between the locating instrument and a cutting guide, when the instrument is inserted in an opening of the cutting guide.

For this purpose, it provides a position locating instrument comprising a base connected to means capable of determining the position of the instrument, a plate moving along with the base for insertion into an opening of a bone cutting guide, and resilient means for compensating for the play between the plate and the guide to prevent a movement of the instrument when it is inserted in the opening.

According to an embodiment of the invention, the resilient play compensation means comprise at least three flexible blades provided to bear against a surface of the opening.

According to an embodiment of the invention, the plate comprises a surface provided to be maintained bearing against a complementary surface of the opening under the action of the flexible blades.

According to an embodiment of the invention, each flexible blade is bent, and is connected to the plate at one end, the opposite end of the blade being provided to come into contact with the surface of the opening.

According to an embodiment of the invention, the end of each flexible blade provided to come into contact with a surface of the opening is tapered.

According to an embodiment of the invention, the locating instrument comprises at least three flexible blades arranged in quincunx.

According to an embodiment of the invention, the plate is formed of a resilient material, the flexible blades being formed in the plate.

According to an embodiment of the invention, the flexible blades are parallel.

According to an embodiment of the invention, the means capable of determining the position of the instrument comprise a rigid body solidly connected to the base on which are arranged back-reflective disks.

According to an embodiment of the invention, the locating instrument comprises markers, each marker being capable of cooperating with means for locating the position of said marker.

The foregoing object, features, and advantages of the present invention, as well as others, will be discussed in detail in the following non-limiting description of specific embodiments in connection with the accompanying drawings, among which:

Figure 1:
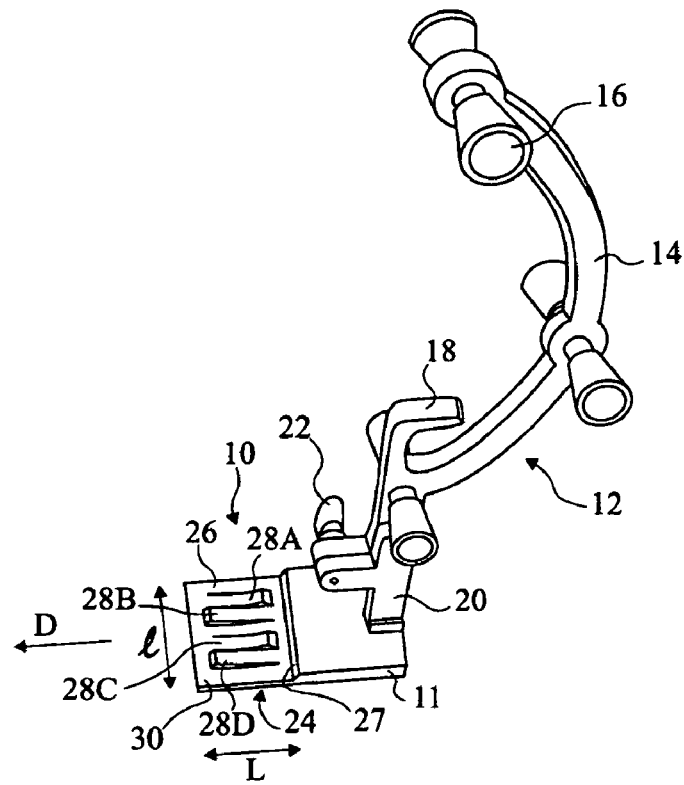
FIG. 1 shows a perspective top view of an example of the forming of a locating instrument according to the invention.
Figure 2:
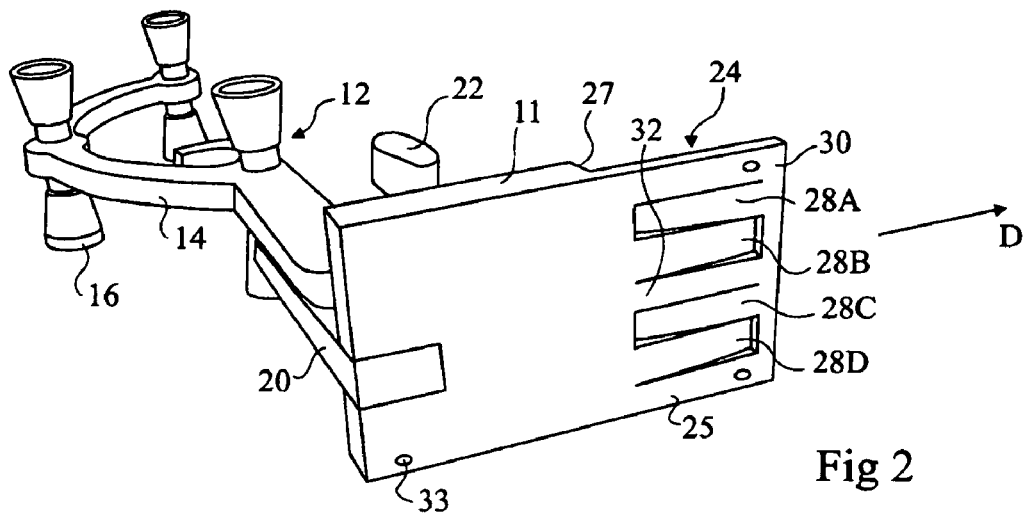
FIG. 2 shows a bottom perspective view of the locating instrument of FIG. 1.

Locating instrument 10 according to the invention has a substantially parallelepipedal base 11 on which is attached a rigid body 12. Rigid body 12 comprises an bow-shaped support 14 on which are arranged six reflective disks 16. Rigid body 12 comprises, at one end of support 14, a protrusion 18 so that support 14 has the general shape of a letter, in the present example, letter "G", which eases the identification of the rigid body. Locating instrument 10 comprises an attachment arm 20 which protrudes from base 11 and on which is attached one end of support 14 of rigid body 12 via attachment means 22, for example, a bolt.

Base 11 prolongs in a substantially parallelepipedal plate 24 which extends along a direction D, represented by an arrow in the drawings. Base 11 and plate 24 are formed of a resilient material, for example, a metal, especially titanium or steel used for medical applications or a plastic matter, especially PEEK (polyetheretherketone) or PET (polyethylene terephtalate), or PVDF (polyvinylidene fluoride). Plate 24 is to be inserted into a substantially parallelepipedal opening of a cutting guide by the edge opposite to base 11 along direction D. Dimensions L and l of the edges of plate 24 respectively extending parallel and perpendicularly to direction D of plate 24 are substantially identical to the corresponding dimensions of the cutting guide opening. Plate 24 comprises a lower surface 25 which prolongs base 11 and an upper surface 26 which defines, along with base 11, a shoulder 27. Shoulder 27 forms a stop on insertion of plate 24 into the cutting guide opening.

Four bent flexible blades 28A to 28D are formed in plate 24 for example by a cutting of portions of plate 24. Each bent blade 28A to 28D extends substantially along direction D and is connected to plate 24 only along an edge perpendicular to direction D. Each blade 28A to 28D is slightly curved and protrudes, at the level of its free end, with respect to upper surface 26 of plate 24.

Among the four bent blades 28A to 28D, two bent blades 28A and 28C have free ends, protruding with respect to upper surface 26 of plate 24, located on the side closest to base 11, while the two other bent blades 28B and 28D have their free ends protruding with respect to upper surface 26 of plate 24 located on the side opposite to base 11.

In the present example of embodiment, the bent blades are arranged in pairs 28A, 28B and 28C, 28D. The two bent blades of a same pair are arranged side by side and are connected to plate 24 by opposite edges. The two pairs of bent blades 28A, 28B and 28C, 28D are surrounded with a portion of plate 24 forming a frame 30 and are separated by a substantially rectilinear portion 32 of plate 24 extending along direction D. Frame 30 and rectilinear portion 32 form a structure giving plate 24 an appropriate stiffness.

The relative position between rigid body 12 and locating instrument 10 is known and is normally set once and for all on assembly of rigid body 12 on locating instrument 10. When locating instrument 10 is inserted into an opening of a bone-cutting guide, the position of rigid body 12 is determined by locating means capable of locating the positions of disks 16. The position of locating instrument 10, and more specifically the position of the plane defined by plate 24, can be easily obtained from the position of rigid body 12.

The relative position between rigid body 12 and locating instrument 10 may vary after several uses. To take such a variation into account, locating cones 33 may be directly provided at the level of locating instrument 10. The positions of locating cones 33 on lower surface 25 of locating instrument 10 are known beforehand. A specific rigid body (not shown), caller a feeler, is used to determine the positions of locating cones 33. For this purpose, the feeler comprises reflective portions and a spherical cap that can be successively introduced into locating cones 33. A locating system enables determining the feeler position. The position of the spherical cap being known with respect to the reflective disks of the feeler, the position of the spherical cap is obtained from that of the feeler, whereby the position of the locating cone in which the spherical cap is introduced is also obtained. Based on the positions of the locating cones, the relative position between lower surface 25 of locating instrument 10 and rigid body 12 is determined. As an example, three locating cones 33 are shown. The position of locating instrument 10 can then be determined regularly, before insertion into the opening of the cutting guide to correct, if needed, the relative position between locating instrument 10 and rigid body 12.

Figure 3:
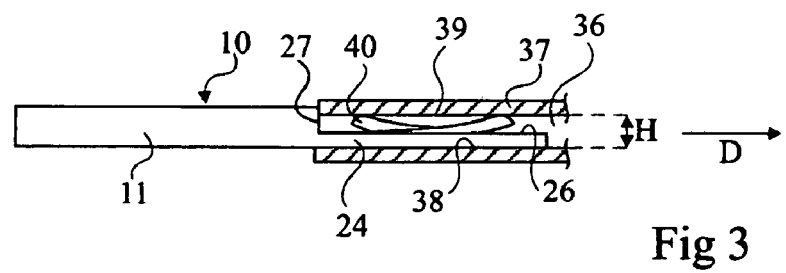
FIG. 3 shows a simplified side view of the locating instrument of FIG. 1 inserted in a cutting guide.

FIG. 3 schematically shows locating instrument 10 having its plate 24 inserted into an opening 36 of a bone cutting guide 37. Opening 36 comprises lower and upper surfaces 38 and 39 which are, when a locating instrument is inserted into opening 36, respectively opposite to lower surface 25 and upper surface 26 of plate 24. Height H of opening 36, that is, the distance separating lower surface 38 from upper surface 39, generally is on the order of from 1 to 2 mm.

Bent blades 28 A to 28 D are flexible enough not to prevent the insertion of plate 24 into opening 36. Bent blades 28 A to 28 D are however rigid enough to maintain lower surface 25 of plate 24 pressed against lower surface 38 of opening 36, the free ends of bent blades 28 A to 28 D bearing against upper surface 39 of opening 36. Bent blades 28 A to 28 D have a sufficient stiffness to provide a sufficient force opposing to a displacement of plate 24 inserted in opening 36 tending to push away lower surface 25 of plate 24 onto lower surface 38 of opening 36. Play between plate 24 and opening 36 is then suppressed. By determining the position of plate 24, the position of the cutting plane is thus directly and accurately obtained The free end of each bent blade 28A to 28D comprises a tapered area 40 capable of cooperating with upper surface 39 of opening 36 to avoid hindering the insertion of plate 24 into opening 36.

According to a variation of the invention, the plate comprises three bent blades, for example, arranged in quincunx or in any other way adapted to the obtaining of an efficient pressing of the plate against the lower surface of the opening.

The locating instrument according to the present invention has many advantages:

First, it enables ensuring the insertion with no play of a plate into an opening of a cutting guide. The determination of the position of the locating instrument then enables accurately obtaining the position of the guide cutting plane.

Second, the suppression of the play is obtained by means of bent blades, the forming of which is particularly simple since they are directly cut in the plate of the locating instrument introduced into the cutting guide opening.

Of course, the present invention is likely to have various alterations and modifications which will readily occur to those skilled in the art. In particular, the number of bent blades may be greater than four. Further, resilient means, for example, formed of bulged flexible blades connected to the plate at their two ends, may be provided instead of or in addition to the bent blades. The central area of each bulged blade comes into contact against the upper surface of the cutting guide opening on insertion of the plate into the opening to maintain the plate bearing against the lower surface of the opening.

The invention claimed is:

1. A position locating instrument (10) for accurately determining the location of a cutting plane, the instrument comprising a base (11) connected to means (12) capable of determining the position of the instrument, a plate (24) moving along with the base for insertion into an opening (36) of a bone cutting guide (37), and resilient means for compensating for the play between the plate and the guide to prevent a movement of the instrument when it is inserted in the opening, the resilient means extending outwardly along only one face of the plate (24) to cause an opposite planar face of the base (11) to lie flush against a complementary planar surface (38) that defines the opening (36), wherein the resilient play compensation means comprise at least three flexible blades (28A, 28B, 28C, 28D) provided to bear against a surface (39) of the opening (36), wherein each flexible blade (28A, 28B, 28C, 28D) is bent, and is connected to the plate (24) at one end, the opposite end of the blade being provided to come into contact with the surface (39) of the opening (36).

2. The instrument of claim 1, wherein the opposite planar face of the base (11) comprises a surface (25) provided to be maintained bearing against the complementary surface (38) of the opening (36) under the action of the flexible blades (28A, 28B, 28C, 28D).

3. The instrument of claim 1, in which the end of each flexible blade (28A, 28B, 28C, 28D) provided to come into contact with a surface (39) of the opening (36) is tapered.

4. The instrument of claim 1, in which the plate is formed of a resilient material, the flexible blades (28A, 28B, 28C, 28D) being formed in the plate (24).

5. The instrument of claim 1, in which the flexible blades (28A, 28B, 28C, 28D) are parallel.

6. The instrument of claim 1, in which the means capable of determining the position of the instrument comprise a rigid body (12) solidly connected to the base (11) on which are arranged back-reflective disks (16).

7. The instrument of claim 1, in which the locating instrument comprises markers (33), each marker being capable of cooperating with means for locating the position of said marker.

* * * * *